United States Patent [19]

DeSimone et al.

[11] Patent Number: 4,670,617
[45] Date of Patent: Jun. 2, 1987

[54] PROPYLATION OF TOLUENE WITH A HIGH SURFACE AREA, ZINC-MODIFIED, CRYSTALLINE SILICA MOLECULAR SIEVE

[75] Inventors: Richard E. DeSimone, Lisle; Muin S. Haddad, Naperville, both of Ill.

[73] Assignee: Amoco Corporation, Chicago, Ill.

[21] Appl. No.: 814,646

[22] Filed: Dec. 30, 1985

[51] Int. Cl.$^4$ .............................................. C07C 2/68
[52] U.S. Cl. .............................................................. 585/467
[58] Field of Search ........................................ 585/467

[56] References Cited

U.S. PATENT DOCUMENTS

| | | | |
|---|---|---|---|
| 4,283,306 | 8/1981 | Herkes | 585/467 |
| 4,291,182 | 9/1981 | Dautzenberg et al. | 585/415 |
| 4,329,328 | 5/1982 | McAnespie et al. | 423/333 |
| 4,417,087 | 11/1983 | Miller | 585/533 |
| 4,423,268 | 12/1983 | Miller | 585/533 |
| 4,423,269 | 12/1983 | Miller | 585/530 |
| 4,482,774 | 11/1984 | Koetsier | 585/467 |
| 4,489,214 | 12/1984 | Butler et al. | 585/467 |

Primary Examiner—Curtis R. Davis
Attorney, Agent, or Firm—Reed F. Riley; William H. Magidson; Ralph C. Medhurst

[57] ABSTRACT

Described are catalyst compositions comprising a high surface area, zinc-modified, crystalline silica molecular sieve, essentially free of aluminum, which has been incorporated into an inorganic matrix; said compositions are useful for hydrocarbon conversion, particularly the propylation of toluene in which they exhibit a very high paraselectivity while making a product containing a high isopropyltoluene/n-propyl-toluene isomer ratio. These catalyst compositions are made from an organic base, a templating material, a zinc ion-affording compound, and an oxide of silicon.

20 Claims, No Drawings

PROPYLATION OF TOLUENE WITH A HIGH SURFACE AREA, ZINC-MODIFIED, CRYSTALLINE SILICA MOLECULAR SIEVE

BACKGROUND OF THE INVENTION

This invention relates to the preparation of catalyst compositions comprising a high surface area, zinc-modified, crystalline silica molecular sieve, essentially free of aluminum, incorporated into an inorganic matrix and to processes for propylating toluene accomplished by contacting toluene and a propylating agent under hydrocarbon conversion conditions with said compositions. More particularly, the invention relates to the preparation without the use of alkali metal ion or ammonia of high surface area, essentially free of aluminum, crystalline silica molecular sieves which have been modified by incorporation of a small amount of zinc, and toluene conversion processes, using catalyst compositions made from the sieves by incorporating such sieves in an inorganic matrix, involving the reaction of propylene and toluene to form a product in which the isopropyltoluene-to-n-propyltoluene isomer ratio is high and the ortho- and metacymene content of the isopropyltoluene fraction is very small compared to the paracymene content. This novel process offers a simple route from toluene to a paracymene product having greatly reduced isomer purification problems.

U.S. Pat. No. 4,254,296 describes a process for the preparation of tertiary olefins employing a crystalline silica having a high specific surface area, modified or unmodified with an oxide of certain metals including zinc capable of entering the silica lattice as a substitute for silicon or as a salt of polysilicic acids. Only the modifying elements chromium, aluminum and beryllium are shown in the Examples. In U.K. Patent Application No. 2,024,790A, high specific surface area crystalline silicas are taught, wherein certain elements, e.g. zinc, are said to have entered the crystal lattice of the silica in place of silicon atoms or in the form of salts of bisilicic or polysilicic acids. A zinc Example is given. These acidic, thermally stable materials are suggested as catalysts for a large number of reactions including the methylation of toluene to xylenes, particularly paraxylene. U.S. Pat. Nos. 4,423,269, 4,423,268 and 4,417,087 describe processes for oligomerization of gaseous olefins over intermediate pore size crystalline silicas including silicalite, chromia silicates (CZM) and U.S. Pat. No. Re. 29,948 organosilicates as described in U.S. Pat. No. Re. 29,948, or silicas containing significant amounts of alumina. Zinc can be incorporated into these materials for activity and stability using standard impregnation and ion exchange techniques. U.S. Pat. No. 4,329,328 teaches the synthesis of small pore "A type" zincosilicate or noncrystalline sodium zincosilicates. U.S. Pat. No. 4,291,182 teaches a process for the preparation of aromatic hydrocarbons and hydrogen from butane over crystalline silicates promoted by zinc incorporated by impregnation or ion exchange. In U.S. Pat. No. 3,894,104, use of a crystalline aluminosilicate zeolite modified by incorporation (exchanged, impregnated and/or vapor deposited) with one of a number of metals including zinc to catalyze aromatization of a heteroatom-substituted hydrocarbon is taught. In U.S. Pat. No. 1,728,732, materials made from a soluble silicate, an alkali metal compound and a heavy metal salt (including zinc salts) which, depending on the proportions used, resemble aluminosilicates were synthesized, and some are said to be useful as catalysts.

SUMMARY OF THE INVENTION

Described herein are catalyst compositions comprising a high surface area, zinc-modified, crystalline silica molecular sieve, essentially aluminum free, incorporated into an inorganic matrix; said compositions when used to catalyze the propylation of toluene are very paraselective at a high isopropyltoluene/n-propyltoluene isomer ratio. These zincosilicate catalyst compositions are made in such a way that the zinc content of the sieve, while small, is incorporated differently in the crystalline lattice than zinc-containing sieves made by ion exchange or impregnation processes.

DETAILED DESCRIPTION OF THE INVENTION

The zincosilicate crystalline molecular sieves of this invention are characterized by the representative X-ray pattern listed in Table A below and by the composition formula:

wherein M is at least one cation, n is the valence of the cation, y is between 4 and about 600 and z is between 0 and about 160. It is believed that the small zinc content of the sieves is at least in part incorporated in the crystalline lattice. Various attempts to remove the zinc from the zincosilicate sieves by exhaustive exchange with sodium, ammonium and hydrogen ions were unsuccessful and therefore, the zinc content is considered nonexchangeable in the instant sieves.

TABLE A

| d-Spacing Å (1) | Assigned Strength (2) | d-Spacing Å (1) | Assigned Strength (2) |
|---|---|---|---|
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | VW | | |

(1) Copper K alpha radiation
(2) VW = very weak; W = weak; M = medium; MS = medium strong; VS = very strong The zincosilicate molecular sieve useful in this invention can be prepared by crystallizing an aqueous mixture, at a controlled pH, of an organic base, a zinc ion-affording material, an oxide of silicon, and an organic template compound.

Typically, the mol ratios of the various reactants can be varied to produce the crystalline zincosilicates of this invention. Specifically, the mol ratios of the initial reactant concentrations are indicated below:

| | Broad | Preferred | Most Preferred |
|---|---|---|---|
| SiO$_2$/ZnO | 4–200 | 10–150 | 20–100 |
| Organic base/SiO$_2$ | 0.5–5 | 0.05–1 | 0.1–0.5 |
| H$_2$O/SiO$_2$ | 5–80 | 10–50 | 20–40 |
| Template/SiO$_2$ | 0–1 | 0.01–0.2 | 0.02–0.1 |

By regulation of the quantity of zinc (represented as ZnO) in the reaction mixture, it is possible to vary the SiO$_2$/ZnO molar ratio in the final product. In general it is desirable to have the zinc content of the zincosilicate sieve of this invention between about 0.1 and about 5 percent by weight of zinc. More preferably, the amount of zinc should be between about 0.2 and about 4 weight percent zinc and, most preferably, between about 0.3 and about 3 weight percent of zinc. Too much zinc in the reaction mixture appears to reduce the sieve crystallinity which reduces the catalytic usefulness of the sieve.

More specifically, the material useful in the present invention is prepared by mixing an organic base, a zinc ion-affording substance, an oxide of silicon, and an organic template compound in water (preferably distilled or deionized). The order of addition usually is not critical although a typical procedure is to dissolve the organic base and the zinc ion-affording substance in water and then add the template compound. Generally, the silicon oxide compound is added with intensive mixing such as that performed in a Waring Blender and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 8.0 to about 12.0; more preferably between about 9.0 and about 11.0 and most preferably between about 9.5 and 10.5.

Examples of oxides of silicon useful in this invention include silicic acid, sodium silicate, tetraalkyl silicates and Ludox, a stabilized polymer of silicic acid manufactured by E. I. DuPont de Nemours & Co. Typically, the oxide of zinc source is a water-soluble zinc compound such as zinc nitrate or zinc acetate or another zinc compound, the anion of which is easily removed during sieve calcination prior to use.

Cations useful in formation of the zincosilicate sieves include the zinc ion and the hydrogen ion. The sieves are prepared directly in the hydrogen form with an organic base such as ethylenediamine. In the case of the instant zincosilicates, some of the zinc may be present in part as a substitute counter ion for the hydrogen ion. The acidity of these sieves is low as measured by the Hammett Ho function which lies in the neighborhood of about +3 to about +6.

Organic templates useful in preparing the crystalline zincosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline zincosilicate molecular sieve can be prepared by crystallizing a mixture of sources for an oxide of silicon, an oxide of zinc, an alkylammonium compound and ethylenediamine such that the initial reactant molar ratios of water to silica range from about 5 to about 80, preferably from about 10 to about 50 and most preferably from about 20 to about 40. In addition, preferable molar ratios for initial reactant silica to oxide of zinc range from about 4 to about 200, more preferably from about 10 to about 150 and most preferably from about 20 to about 100. The molar ratio of ethylenediamine to silicon oxide should be about above about 0.05, typically below about 5, preferably between about 0.05 and about 1.0 and most preferably between about 0.1 and about 0.5. The molar ratio of alkylammonium compound, such as tetra-n-propylammonium bromide, to silicon oxide can range from 0 to about 1 or above, typically above about 0.005, preferably about 0.01 to about 0.2, most preferably 0.02 to about 0.1.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours. The zincosilicate sieves thus made, generally have a surface area greater than about 300 sq. meters per gram as measured by the BET procedure.

The zincosilicate sieve useful in this invention is admixed with or incorporated within various binders or matrix materials depending upon the intended process use. The crystalline zincosilicates are combined with active or inactive materials, synthetic or naturally-occurring zeolites, as well as inorganic or organic materials which would be useful for binding the zincosilicate. Well-known materials include silica, silica-alumina, alumina, magnesia, titania, zirconia, alumina sols, hydrated aluminas, clays such as bentonite or kaolin, or other binders well-known in the art. Typically, the zincosilicate is incorporated within a matrix material by blending with a sol of the matrix material and gelling the resulting mixture or slurrying the sieve with the matrix material and drying. Also, solid particles of the zincosilicate and matrix material can be physically admixed. Typically, such zincosilicate compositions can be pelletized or extruded into useful shapes. The crystalline zincosilicate content can vary anywhere from a few up to 100 wt. % of the total composition. Catalytic compositions can contain about 0.1 wt. % to about 100 wt. % crystalline zincosilicate material and preferably contain about 10 wt. % to about 95 wt. % of such material and most preferably contain about 20 wt. % to about 80 wt. % of such material.

More specifically, catalytic compositions comprising the crystalline zincosilicate material of this invention and a suitable matrix material are formed by adding a finely-divided crystalline zincosilicate sieve to an aqueous sol or gel of the matrix material, such as PHF Alumina made by American Cyanamid Co. The resulting mixture is thoroughly blended and gelled, typically by adding a material such as ammonium hydroxide. The resulting gel is dried below about 200° C., more preferably between about 100° C. and about 150° C. and calcined between about 350° C. and about 700° C. to form a catalyst composition in which the crystalline zincosilicate sieve is distributed throughout the matrix material.

Alternatively, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° C. to about 150° C. and then calcined at between about 350° C. and about 700° C., more preferably between about 400° C. to about 650° C.

The catalyst compositions of this invention appear to be more paraselective for the propylation of toluene when matrixed by the slurry technique rather than the gel technique, both of which are described immediately above.

Catalyst compositions of this invention are useful in hydrocarbon conversion reactions. A particularly useful reaction is alkylation of aromatics and especially propylation of toluene.

Propylation of toluene in the presence of the above-described catalyst compositions is effected by contact of the toluene with propylene, preferably in the gas phase, at a temperature between about 200° C. and about 600° C. and preferably between about 250° C. and about 400° C. The reaction generally takes place at atmospheric pressure, but the pressure may be within the approximate range of about 1 atmosphere to about 2000 psig. The molar ratio of toluene to propylene employed is within the approximate range of about 0.5 to about 50, more preferably about 2 to about 20. Reaction is suitably accomplished utilizing a weight hourly space velocity of between about 0.1 and about 100 and preferably between about 0.5 and about 50. The reaction product consisting selectively of paracymene with comparatively smaller amounts of other isopropyltoluenes and n-propyltoluenes may be separated, if required, by any suitable means such as fractionation.

The following Examples will serve to illustrate certain specific embodiments of the hereindisclosed invention. These Examples should not, however, be construed as limiting the scope of the novel invention as there are many variations which may be made thereon without departing from the spirit of the disclosed invention, as those of skill in the art will recognize.

EXAMPLES

General

The reactions in the hydrocarbon conversion Examples below were carried out in a stainless steel reactor of plug-flow design. Reactants were mixed and then fed into a preheater packed with inert Denstone packing and passed into a ½-inch O.D.×5-inch reactor tube filled with a 3-5 g catalyst composition charge. The entire reactor and preheater assembly was supported in a fluidized sand bath maintained at reaction temperature. Product was collected in a cooled vessel as it dripped from the reactor and analyzed by gas chromatography on a 60-meter fused silica capillary column. All hydrocarbon isomer amounts are given in percents by weight.

EXAMPLE 1

Zincosilicate Sieve

A reaction mixture composed of 9000 ml of water, 800 ml of ethylenediamine, 240 g of tetrapropylammonium bromide, 60 g of $Zn(CH_3COO)_2 \cdot 4H_2O$ and 3000 g Ludox HS-40, was prepared. All reactants except the Ludox HS-40 were introduced into a 5-gallon autoclave in the order given above. They were mixed until the solution was clear. The Ludox HS-40 was rapidly added. The digestion temperature was set at 165° C. and mixing speed at about 500 rpm. The digestion was continued for 4 days. The slurry was then filtered and the product washed thoroughly with distilled water and dried at 130° C. for 16 hours. X-ray analysis shows the product is over 90% crystalline and has a surface area measured by BBT of 331 sq. in. per gram. Analysis of the $SiO_2$ and Zn contents gave 95.2 and 1.07 weight percents, respectively. The average pore volume is 0.0657 cc per gram. This material had the following X-ray diffraction pattern.

TABLE A

| d-Spacing Å (1) | Assigned Strength (2) | d-Spacing Å (1) | Assigned Strength (2) |
|---|---|---|---|
| 11.337 | VS | 3.051 | VW |
| 10.209 | MS | 2.998 | VW |
| 10.104 | MS | 2.968 | VW |
| 9.875 | W | 2.936 | VW |
| 9.109 | VW | 2.872 | VW |
| 8.139 | VW | 2.794 | VW |
| 7.518 | VW | 2.741 | VW |
| 7.144 | VW | 2.688 | VW |
| 6.761 | VW | 2.620 | VW |
| 6.411 | VW | 2.610 | VW |
| 6.047 | W | 2.596 | VW |
| 5.987 | VW | 2.571 | VW |
| 5.750 | W | 2.560 | VW |
| 5.617 | VW | 2.522 | VW |
| 5.577 | VW | 2.495 | VW |
| 5.415 | VW | 2.481 | VW |
| 5.379 | VW | 2.422 | VW |
| 5.172 | VW | 2.401 | VW |
| 5.064 | VW | 2.205 | VW |
| 5.010 | VW | 2.185 | VW |
| 4.910 | VW | 2.131 | VW |
| 4.640 | VW | 2.015 | VW |
| 4.481 | VW | 1.994 | VW |
| 4.384 | VW | 1.956 | VW |
| 4.282 | VW | 1.917 | VW |
| 4.101 | VW | 1.880 | VW |
| 4.028 | VW | 1.866 | VW |
| 3.872 | MS | 1.772 | VW |
| 3.842 | W | 1.764 | VW |
| 3.829 | M | 1.752 | VW |
| 3.769 | W | 1.675 | VW |
| 3.757 | VW | 1.671 | VW |
| 3.733 | M | 1.666 | VW |
| 3.673 | VW | 1.464 | VW |
| 3.646 | VW | 1.449 | VW |
| 3.612 | VW | 1.442 | VW |
| 3.493 | VW | | |
| 3.453 | VW | | |
| 3.412 | VW | | |
| 3.367 | VW | | |
| 3.330 | VW | | |
| 3.315 | VW | | |

TABLE A-continued

| d-Spacing Å (1) | Assigned Strength (2) | d-Spacing Å (1) | Assigned Strength (2) |
| --- | --- | --- | --- |
| 3.265 | VW | | |
| 3.067 | VW | | |

(1) Copper K alpha radiation
(2) VW = very weak; W = weak; M = medium; MS = medium strong; VS = very strong

EXAMPLE 2

Catalyst Compositions: Preparative Technique Gel

A 10 g portion of the sieve of Example 1 was placed in a mechanical mixing bowl with 15 ml of water. To this was added 148.96 g of 10.07% PHF alumina sol. The mixture was slowly stirred for about 15 minutes at which time 22 ml of 15 M NH₄OH was added. The resulting mixture solidified, but continued stirring resulted in a somewhat more workable, less thick gel. This material was dried at 130° C. for about 16 hrs and then calcined at 600° C.

EXAMPLE 3

Catalyst Compositions: Preparative Technique Slurry

A 10 g portion of the sieve of Example 1 was placed in a mechanical mixing bowl along with 15 g of alpha alumina monohydrate (Conoco Catapal SB Alumina) and 57 ml of 5% acetic acid. The mixture was stirred for about 15 minutes until a uniform consistency had been achieved. This material was dried at 130° C. for about 16 hrs and calcined at 600° C.

COMPARATIVE EXAMPLE 4

A 2.8 g portion of the catalyst composition of Example 2 was placed in the reactor and heated to 300° C. under a stream of argon. Toluene was then fed to the reactor at 0.21 ml/min. and ethylene at 5.7 ml/min. (about an 8:1 toluene:ethylene mol ratio). Analysis of the product shows ethyltoluenes to be the dominant product. Product data are presented in Table I below.

COMPARATIVE EXAMPLE 5

A 4.2 g portion of the catalyst composition of Example 3 was placed in the reactor. Toluene and ethylene were fed as in Example 4. Product data are given in Table I below.

EXAMPLE 6

A 3.3 g portion of the catalyst composition of Example 2 was placed in the reactor. Toluene was then fed to the reactor at 0.21 ml/min. and propylene at 5.9 ml/min. (about an 8:1 toluene:propylene mol ratio). Analysis of the product shows isopropyltoluenes to be the main product with lesser amounts of n-propyltoluenes. Product data are presented in Table II below.

EXAMPLE 7

A 4.4 g portion of the catalyst composition of Example 3 was placed in the reactor. Toluene and propylene were fed as in Example 6. Product data are given in Table II below.

EXAMPLE 8

The catalyst composition used in Example 7 was recalcined and the propylation conditions used were the same. Product data are given in Table II below.

TABLE I

| Example No. | Ethyltoluene Selectivity | | | Conversion % | Reaction Temp. °C. |
| --- | --- | --- | --- | --- | --- |
| | % o- | % m- | % p- | | |
| 4 | <.05 | 53 | 47 | 40 | 300 |
| 4 | 3.4 | 60.6 | 36 | 80 | 350 |
| 4 | 4 | 60 | 36 | 90 | 375 |
| 5 | <.05 | 30 | 70 | 10 | 300 |
| 5 | <.05 | 25 | 75 | 25 | 350 |
| 5 | <.05 | 37 | 63 | 60 | 400 |
| 5 | <.05 | 43 | 57 | 70 | 450 |

TABLE II

| Example No. | Cymenes Selectivity | | | Iso/Nor | Conversion % | Reaction Temp. °C. |
| --- | --- | --- | --- | --- | --- | --- |
| | % o- | % m- | % p- | | | |
| 6 | 7.8 | 32.8 | 59.4 | 3.2:1 | 50 | 300 |
| 6 | 6.3 | 38.9 | 54.8 | 1.2:1 | 40 | 350 |
| 6 | 7.2 | 59.8 | 33.0 | .5:1 | 30 | 400 |
| 6 | 6.8 | 63.9 | 29.3 | .5:1 | 25 | 450 |
| 7 | <.05 | 2.0 | 98.0 | 11:1 | 50 | 300 |
| 7 | <.05 | 3.0 | 97.0 | 4.5:1 | 30 | 350 |
| 7 | <.05 | 3.5 | 96.5 | 4.5:1 | 25 | 375 |
| 7* | <.05 | 11.4 | 88.6 | 33:1 | 15 | 250 |
| 8 | <.05 | 3 | 97 | 2.5:1 | 80 | 300 |
| 8 | <.05 | 2 | 98 | 8.6:1 | 60 | 300 |
| 8 | <.05 | 2 | 98 | 8.6:1 | 60 | 300 |
| 8 | <.05 | 2 | 98 | 7.1:1 | 50 | 315 |
| 8 | <.05 | 2.3 | 97.7 | 4.8:1 | 30 | 350 |
| 8 | <.05 | 2.9 | 97.1 | 3:1 | 25 | 375 |

*This catalyst composition had lost most of its activity when the temperature was lowered to 250° C.

What is claimed is:

1. A process comprising contacting toluene and propylene under alkylation conditions with a catalyst composition comprising a high surface area, crystalline silica molecular sieve, essentially aluminum free and containing between about 0.1 weight percent and about 5 weight percent nonexchangeable zinc, composited in an inorganic matrix, said sieve made by crystallization from an aqueous solution containing an organic base, an organic templating material, a zinc ion-affording material and an oxide of silicon and providing an X-ray pattern comprising the following X-ray diffraction lines and assigned strengths:

| Interplanar Spacing d, Å | Assigned Strength | Interplanar Spacing d, Å | Assigned Strength |
| --- | --- | --- | --- |
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | W | | |

2. The process of claim 1 wherein the amount of zinc in said crystalline silica molecular sieve is between about 0.2 and about 4 weight percent.

3. The process of claim 1 wherein the amount of zinc in said crystalline silica molecular sieve is between about 0.3 and about 3 weight percent.

4. The process of claim 1 wherein said inorganic matrix is silica, silica-alumina or alumina.

5. The process of claim 2 wherein said inorganic matrix is silica, silica-alumina or alumina.

6. The process of claim 3 wherein said inorganic matrix is silica, silica-alumina or alumina.

7. The process of claim 1 wherein said inorganic matrix is alumina.

8. The process of claim 2 wherein said inorganic matrix is alumina.

9. The process of claim 3 wherein said inorganic matrix is alumina.

10. The process of claim 7 wherein said catalyst composition is made by a process comprising slurrying together said sieve and said inorganic matrix in a liquid, removing said liquid and calcining the result between about 350° C. and about 700° C.

11. The process of claim 8 wherein said catalyst composition is made by a process comprising slurrying together said sieve and said inorganic matrix in a liquid, removing said liquid and calcining the result between about 350° C. and about 700° C.

12. The process of claim 9 wherein said catalyst composition is made by a process comprising slurrying together said sieve and said inorganic matrix in a liquid, removing said liquid and calcining the result between about 350° C. and about 700° C.

13. A process comprising contacting toluene and propylene under alkylation conditions with a catalyst composition comprising a high surface area, crystalline silica molecular sieve, essentially aluminum free and containing between about 0.2 weight percent and about 4 weight percent nonexchangeable zinc, composited in an inorganic matrix, said sieve made by crystallization from a solution containing ethylenediamine, tetrapropylammonium bromide, zinc acetate or nitrate, and an oxide of silicon, and providing an X-ray pattern comprising the following X-ray diffraction lines and assigned strengths:

| Interplanar Spacing d, Å | Assigned Strength | Interplanar Spacing d, Å | Assigned Strength |
|---|---|---|---|
| 11.34 ± 0.20 | VS | 3.87 ± 0.10 | MS |
| 10.21 ± 0.20 | MS | 3.84 ± 0.10 | W |
| 10.10 ± 0.20 | MS | 3.83 ± 0.10 | M |
| 9.88 ± 0.20 | W | 3.77 ± 0.10 | W |
| 6.05 ± 0.20 | W | 3.73 ± 0.10 | M |
| 5.75 ± 0.20 | W | | |

14. The process of claim 13 wherein the amount of zinc in said crystalline silica molecular sieve is between about 0.3 and about 3 weight percent.

15. The process of claim 13 wherein said inorganic matrix is silica, silica-alumina or alumina.

16. The process of claim 14 wherein said inorganic matrix is silica, silica-alumina or alumina.

17. The process of claim 13 wherein said inorganic matrix is alumina.

18. The process of claim 14 wherein said inorganic matrix is alumina.

19. The process of claim 17 wherein said catalyst composition is made by a process comprising slurrying together said sieve and said inorganic matrix in a liquid, removing said liquid and calcining the result between about 350° C. and about 700° C.

20. The process of claim 18 wherein said catalyst composition is made by a process comprising slurrying together said sieve and said inorganic matrix in a liquid, removing said liquid and calcining the result between about 350° C. and about 700° C.

* * * * *